United States Patent
Ishigooka et al.

(12) 
(10) Patent No.: US 6,714,813 B2
(45) Date of Patent: Mar. 30, 2004

(54) METHOD FOR MEASURING THE DEGREE OF EDEMA AND APPARATUS USING THE SAME

(75) Inventors: Maki Ishigooka, Omagari (JP); Yoshinori Fukuda, Akita (JP)

(73) Assignee: Tanita Corporation, Tokyo (JP)

( * ) Notice: Subject to any disclaimer, the term of this patent is extended or adjusted under 35 U.S.C. 154(b) by 202 days.

(21) Appl. No.: 09/759,320

(22) Filed: Jan. 16, 2001

(65) Prior Publication Data

US 2001/0020138 A1 Sep. 6, 2001

(30) Foreign Application Priority Data

Jan. 21, 2000 (JP) .................................... 2000-012372

(51) Int. Cl.[7] .............................................. A61B 5/05
(52) U.S. Cl. ..................... 600/547; 600/300; 600/372; 600/399; 600/548; 600/544; 600/322
(58) Field of Search ............................. 600/547, 300, 600/372, 393, 399, 548, 544, 322

(56) References Cited

U.S. PATENT DOCUMENTS 5,807,270 A    9/1998   Williams 6,080,106 A  * 6/2000   Lloyd et al. ................. 600/300
6,496,725 B2 * 12/2002  Kamada et al. ............. 600/547

FOREIGN PATENT DOCUMENTS

JP           10-000185           1/1998

OTHER PUBLICATIONS

Hiroshi Kanai, et al., "Electrical measurement of fluid distribution in legs and arms", Medical Progress through Technology 12, pp. 159–170, (1987).

* cited by examiner

Primary Examiner—Shawntina Fuqua
(74) Attorney, Agent, or Firm—McDermott, Will & Emery

(57) ABSTRACT

Disclosed is an edema measuring method comprising the steps of: putting at least two pairs of electrodes on different locations selected in the body; making an alternating current to flow in the body via one pair of electrodes; measuring voltage appearing between the other pair of electrodes; calculating impedance on the basis of the supplied alternating current and the measured voltage; and calculating an index value representing the degree of edema on the basis of the impedance. Also, an apparatus using the method is disclosed.

21 Claims, 13 Drawing Sheets

FIG. 3 yy/mm/dd    hh:mm

1 : MEASUREMENT

2 : GRAPHICAL REPRESENTATION

3 : COMMUNICATION

FIG. 4 yy/mm/dd    hh:mm

| | |
|---|---|
| SEX | MALE/FEMALE |
| AGE | OOO |
| HEIGHT | OOO.Ocm |
| WEIGHT | OOO.Okg |

FIG. 5
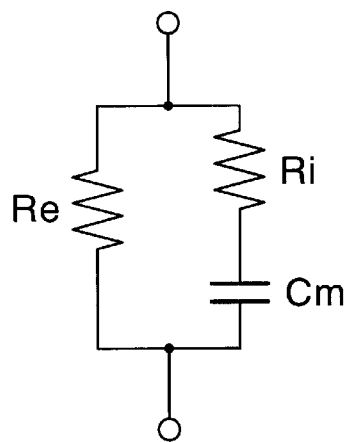
FIG. 6
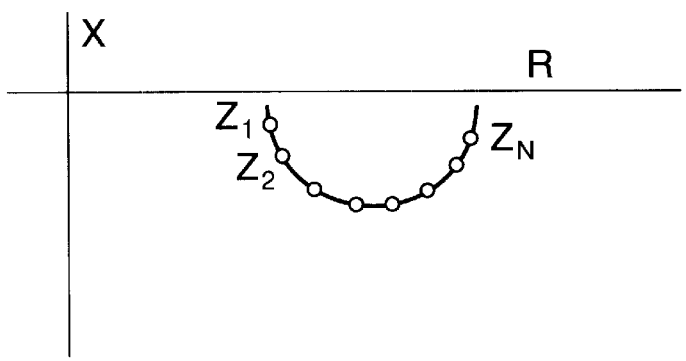
FIG. 7
```
yy/mm/dd    hh:mm
DEGREE OF EDEMA    0.09
    WEIGHT        65.0kg
```

METHOD FOR MEASURING THE DEGREE OF EDEMA AND APPARATUS USING THE SAME

BACKGROUND OF THE INVENTION

1. Field of the Invention

The present invention relates to a method for measuring the degree of edema which appears in one's body and an apparatus using the same.

2. Prior Art

A swell caused by Intra-cellular or extra-cellular accumulation of interstitial fluid and lymph is called "edema". Appearing edema everywhere in a whole body may be realized as a symptom of diseases such as heart disease, kidney disease, liver disease, and such like. Therefore, measuring the degree of edema exactly is very useful in diagnosing or in monitoring patients' condition.

The degree of edema, however, cannot be measured by ordinary people. Patients suffering from heart disease, kidney disease, liver disease or such like can monitor their weights regularly at home. The incremental weight, however, cannot be used as indicating the increment of water content in the body. The degree of edema, therefore, cannot be measured in terms of incremental weight. Specifically the body weight (Wt) represents a sum of weights of different body compositions, such as fat, fat free mass and total body water including intra-cellular water (ICW) and extra-cellular water (ECW). The weight of each body composition, however, cannot be separated from the weight of the body.

One object of the present invention is to provide a method of measuring the degree of edema with accuracy and easiness.

Another object of the present invention is to provide an apparatus which is capable of measuring the degree of edema with accuracy and easiness.

SUMMARY OF THE INVENTION

A method for measuring the degree of edema of a person according to the present invention comprises the steps of: putting at least two pairs of electrodes on different locations selected in the body of the person; supplying alternating current to one pair of electrodes; measuring voltage appearing between the other pair of electrodes; calculating impedance on the basis of the supplied alternating current and the measured voltage; and calculating an index value representing the degree of edema on the basis of the impedance.

Said alternating current may include a plurality of alternating current components of different frequencies, which are supplied one after another to said one pair of electrodes; voltage appearing between said the other pair of electrodes may be measured every time when an alternating current component of selected frequency is supplied; the impedance value may be calculated on the basis of each alternating current component and corresponding voltage; and the index value of edema may be calculated on the basis of the so calculated impedance values.

The index value of edema thus calculated may be a ratio of intra-cellular water to extra-cellular water or inversely, or a ratio of extra-cellular water to total body water or inversely.

An alternating current of single frequency may be supplied to said one pair of electrodes; and the index value of edema may be calculated on the basis of the phase difference between the alternating current and the voltage, and the resistance value calculated from the alternating current and the voltage.

An apparatus which is capable of measuring the degree of edema of a person according to the present invention comprises: at least two pairs of electrodes to be put on selected locations in the body of the person; an alternating current supplying device which supplies alternating current to one pair of electrodes; a voltage measuring device which measures the voltage appearing between the other pair of electrodes; and an arithmetic unit which calculates impedance on the basis of the supplied alternating current and the determined voltage, and calculates an index value representing the degree of edema on the basis of the so calculated impedance.

The alternating current supplying device may supply a plurality of alternating currents of different frequencies to said one pair of electrodes; and the voltage measuring device may measure the voltage appearing between said the other pair of electrodes every time when an alternating current of selected frequency is supplied, allowing the arithmetic unit to calculate the impedance values on the basis of each alternating current and corresponding voltage and to calculate the index value of edema on the basis of the so calculated impedance values.

The index value of edema thus calculated may be a ratio of intra-cellular water to extra-cellular water or inversely, or a ratio of extra-cellular water to total body water or inversely.

The edema measuring apparatus may further comprise a phase difference measuring device which measures the phase difference between the supplied alternating current and the measured voltage, whereby the arithmetic device may calculate the index value of edema on the basis of the phase difference and the resistance value calculated from the alternating current and the voltage provided that an alternating current of single frequency is supplied to said one pair of electrodes.

The edema measuring apparatus may further comprise an estimating device which determines what stage of edema the person has from the calculated index value of edema and other relevant data to be referred to.

Said estimating device may further determine whether the amount of food has been regulated well from the calculated index value of edema and other relevant data to be referred to.

Said other relevant data may be body weight or fat free mass of the person.

The edema measuring apparatus may further comprise an estimating device which determines what stage of edema the person has by comparing the calculated index value of edema with a reference value which represents the index value of edema in normal physical condition.

The edema measuring apparatus may further comprise an estimating device which determines what stage of edema the person has by comparing the present index value of edema with the average of the index values of edema already calculated.

The edema measuring apparatus may further comprise a display which shows the calculated index value of edema and/or the determined stage of edema the person has.

Said display may show a series of index values of edema already calculated, representing how the index value of edema has been varied.

Said display may show averages of index values of edema, each average representing the average of the index values calculated in each of 10 to 15 equi-divisions into which the length of time spanning from the outset to the latest measurement is divided.

The edema measuring apparatus may further comprise a communication device which transmits to other data processors at least one sort of information selected among measured voltage, measured phase difference, some derivations therefrom, calculated index value of edema, determined stage of edema the person has, and personal particulars.

Said communication device may receive the results of a given process executed on said information in said other data processors.

The edema measuring apparatus may further comprise a writing device which writes one sort of information selected among measured voltage, measured phase difference, some derivations therefrom, calculated index value of edema, determined stage of edema the person has, and personal particulars.

Other objects and advantages of the present invention will be understood from the following description of some preferred embodiments, which are shown in accompanying drawings:

FIG. 3 illustrates a screen image initially appearing in the display of the apparatus of FIG. 1;

FIG. 4 illustrates a screen image in inputting personal particulars;

FIG. 5 shows an equivalent circuit representing bioelectrical impedance;

FIG. 6 shows one example of locus which the points of bioelectrical impedance vectors follow;

FIG. 7 illustrates a screen image showing the results of measurement effected by the edema measuring apparatus;

DESCRIPTION OF PREFERRED EMBODIMENTS

The present invention can be reduced to practice in two different modes: one uses plural alternating currents of different frequencies, and the other uses an alternating current of single frequency. The latter is simple in structure, and is easy in operation. The following description begins with the former as a first embodiment, the latter being described later as a second embodiment.

Figure 1:
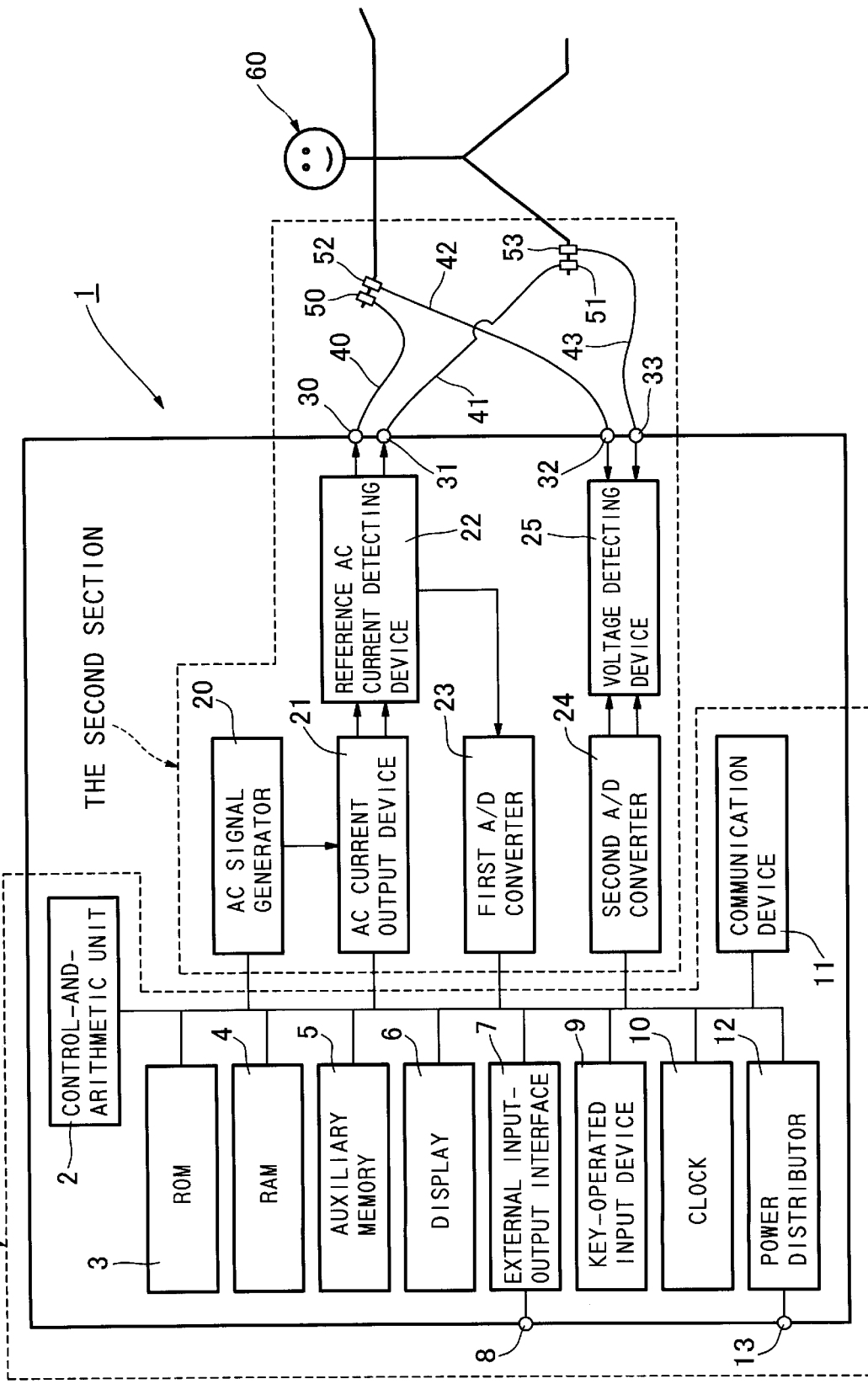
FIG. 1 illustrates major parts of an edema measuring apparatus according to a first embodiment of the present invention.

FIG. 1 illustrates major components of an edema measuring apparatus according to the first embodiment. As seen from the drawing, the major components are shown as being grouped in two sections (broken lines): the first section takes the roles of control, arithmetic operation, and input-output of data whereas the second section takes the roles of measurement of bioelectrical impedance and A/D conversion.

The first section includes a control-and-arithmetic unit 2, a ROM 3, a RAM 4, a nonvolatile auxiliary memory 5, a display 6, an external input-output interface 7, an external interface terminal 8, a key-operated input device 9, a clock 10, a modem built-in communication device 11, a power distributor 12 and a power supply terminal 13.

The control-and-arithmetic unit 2 performs the controlling of measurement and the processing of the results of measurement. The ROM 3 stores programs and some parameters for control and arithmetic operations. The RAM 4 temporarily stores the results of measurement or acquired data, the results of arithmetic operations, the data derived from external devices, selected programs and such like. The auxiliary memory 5 stores the acquired data, the results of arithmetic operations, some parameters relating to measurements and such like. The display 6 shows some helpful guidance of operation, the progressing of measurement, the results of measurements, the results of arithmetic operations and such like. The external input-output interface 7 permits some parameters relating to measurement and the results of measurements to be transferred to external devices, and inversely it permits some parameters relating to measurement, instructions for controlling measurement, control programs and such like to be supplied from external devices. The external input-output interface 7 can be connected to given external devices via the external interface terminal 8. The key-operated input device 9 inputs data such as instructions for controlling the present apparatus and personal particulars required for measurement. The clock 10 measures on what day and time each measurement is made, recording such day and time for later use. The communication device 11 transmits the results of measurements and some derivations therefrom to other computers via telephone lines. The power distributor 12 is supplied with electric power from an external power supply via the terminal 13 to distribute the electric power to each component of the edema measuring apparatus.

The second section includes an AC signal generator 20, an AC current output device 21, a reference AC current detecting device 22, paired AC current output terminals 30 and 31, paired measurement current applying electrodes 50 and 51, paired measurement cables 40 and 41 which connects the terminals 30 and 31 to the electrodes 50 and 51 respectively, a first A/D converter 23, paired voltage measurement terminals 32 and 33, paired voltage measurement electrodes 52 and 53, paired measurement cables 42 and 43 which connects the terminals 32 and 33 to the electrodes 52 and 53 respectively, a voltage detecting device 25 and a second A/D converter 24.

The AC signal generator 20 provides a plurality of alternating current signals of different frequencies which are determined according to the control program stored in the ROM 3 or the RAM 4. Such alternating currents of different frequencies are directed to the AC current output device 21, in which their effective values are modified according to the control program stored in the ROM 3 or the RAM 4, and then the so modified alternating currents are directed to the reference AC current detecting device 22. The device 22 provides the alternating currents of different frequencies sequentially at its output terminals 30 and 31, so that a selected alternating current may be made to flow in one's body via the paired measurement cables 40 and 41 and the paired electrodes 50 and 51. At the same time the device 22 detects the quantity of the alternating current flowing in the body, the analogue value of which alternating current is converted to a corresponding digital value in the first A/D converter 23. On the other hand the voltage detecting device 25 receives at its input terminals 32 and 33 a signal representing the voltage appearing between the paired voltage measurement electrodes 52 and 53, which are applied to two points selected on the body 60, via the measurement cables 42 and 43. Thus, the voltage is detected in the voltage detecting device 25, and the so detected voltage is converted to a corresponding digital value in the second A/D converter 24.

Bioelectrical impedance appearing between two points selected on one hand and one foot of the person 60 in lying posture is measured in the conventional way well known per se. One of the measurement current applying electrodes 50 is applied to a selected inter-finger joint point of the back of the hand and the other electrode 51 is applied to a selected inter-finger joint point of the instep of the foot. One of the voltage measurement electrodes 52 is applied to a selected point of the wrist and the other electrode 53 is applied to a selected point of the ankle.

Figure 2:
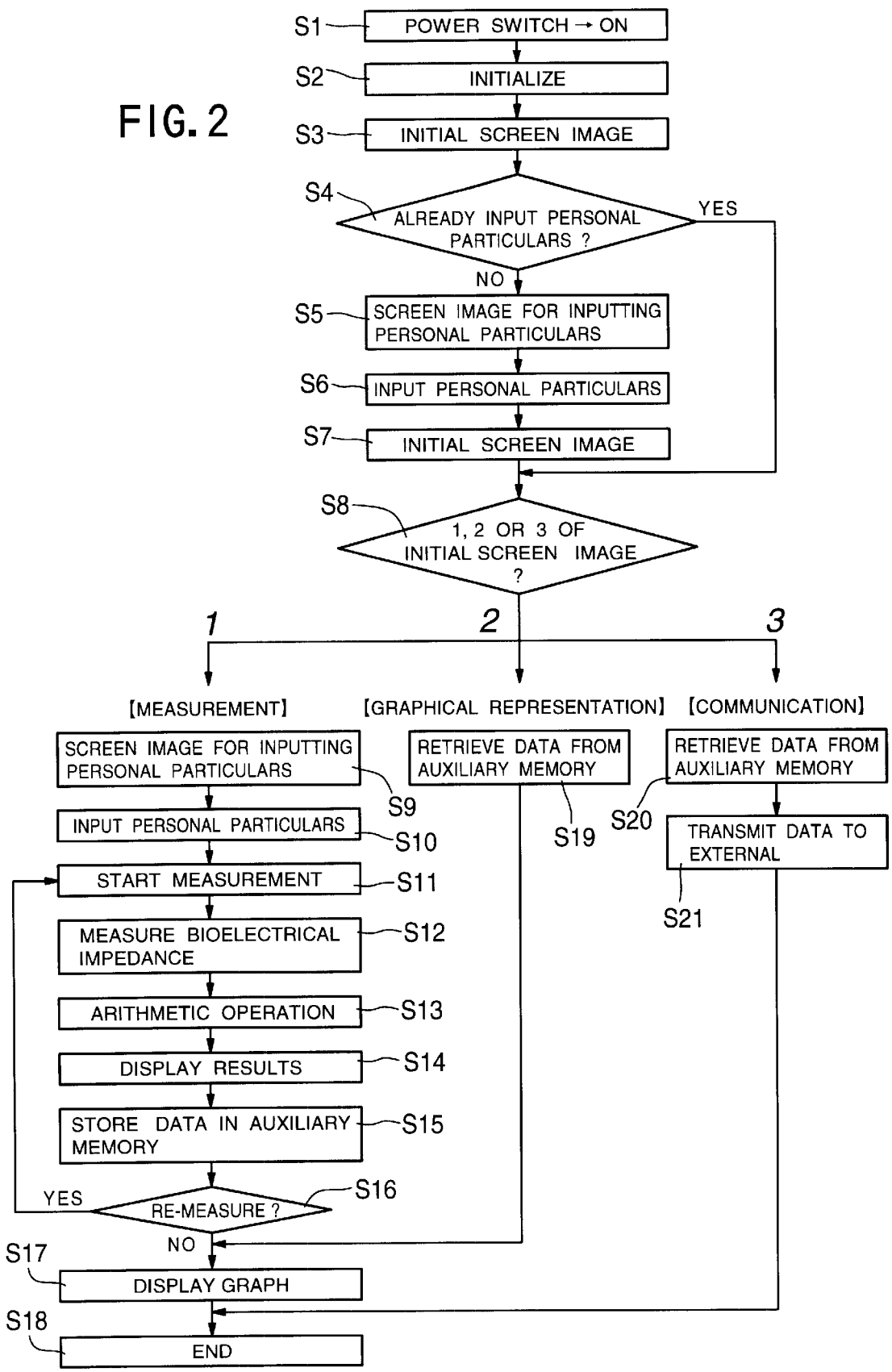
FIG. 2 is a flowchart showing a series of actions taken for measuring the degree of edema in the body.

FIG. 2 shows a flowchart illustrating a series of actions taken for measuring the degree of edema of a person. The power switch is depressed at step 1, thus initializing the edema measuring apparatus 1 at step 2. Then, the screen image of FIG. 3 appears on the display 6 at step 3. At step 4 a check is made in terms of whether personal particulars including sex, height, body weight and age of the person have been already input. In the affirmative case the proceeding goes to step 8. In the negative case the proceeding goes to step 5, in which the blanked screen image of FIG. 4 appears on the display 6. At step 6 when the blanks are filled with personal particulars with the aid of the key-operated input device 9, the initial screen image of FIG. 3 appears again at step 7, and then the proceeding goes to step 8. At step 8 the person can select a desired item among "measurement", "graphical representation" and "communication" simply by depressing the keys representing numbers 1, 2 and 3 allotted to such functions in the screen of FIG. 3. Specifically when the key "1" is depressed, the screen image of FIG. 4 appears with its blanks filled with personal particulars at step 9. Such personal particulars can be modified as desired by using the key-operated input device 9 at step 10. Then, the proceeding goes to step 11, where measurement of bioelectrical impedance is made to start by depressing the measurement onset key. The measurement current applying electrodes 50 and 51 and the voltage measuring electrodes 52 and 53 should be applied to selected points of the person 60 before depressing the measurement onset key.

At step 12 the bioelectrical impedance is measured as follows. The AC signal generator 20 produces automatically an alternating current signal having a frequency determined in terms of some measurement parameters. These parameters are pre-stored in the ROM 3, or are stored in the RAM 4 after being transferred from the auxiliary memory 5 or the external input-output interface 7. The alternating current of the so determined frequency is directed to the AC current output device 21, where the effective value of the alternating current is modified according to similar measurement parameters. The so controlled alternating current passes through the reference current detecting device 22, the paired AC current output terminals 30 and 31, the paired measurement cable 40 and 41 and the paired measurement current applying electrodes 50 and 51, flowing in the body 60. Then, the quantity of the alternating current flowing in the body 60 is detected by the reference AC current detecting device 22, the analog value of which alternating current is converted to a corresponding digital value in the first A/D converter 23. The digital value is stored in the RAM 4.

On the other hand, a signal representing the voltage appearing between the paired voltage measurement electrodes 52 and 53, which are applied to two points selected on the body 60, is supplied to the voltage detecting device 25 via the paired measurement cable 42 and 43 and the paired voltage measurement terminals 32 and 33. In the device 25 the voltage appearing between the paired electrodes 52 and 53 is detected, and the so detected voltage is converted to a corresponding digital value in the second A/D converter 24, so that the digital value is stored in the RAM 4. The arithmetic-and-control unit 2 calculates the bioelectrical impedance based on the digital values from the first and second converters 23 and 24. Repeating the above mentioned procedure, a series of bioelectrical impedance values are provided by using alternating currents of different frequencies Fi (i=1, 2, ..., n) one after another.

Now, the proceeding goes to step 13, in which arithmetic operations using the bioelectrical impedance values measured at step 12 are executed to calculate an equation representing a locus of bioelectrical impedance vectors, which locus is drawn by plotting their points, and some variables relating to the so calculated locus.

Ordinarily a bioelectrical impedance can be expressed equivalently by a lumped-constant circuit, which consists of extra-cellular water resistance Re, intra-cellular water resistance Ri, and cell membrane capacitance Cm as shown in FIG. 5. The locus of bioelectrical impedance values actually measured, however, is not in conformity with a semicircular locus drawn theoretically from the impedance values, which are determined from the equivalent circuit whose components are given in the form of lumped constant elements. Because all cells of a living body cannot be expressed by one and same equivalent circuit; specifically each cell has a different shape and characteristic, and should be expressed by a different equivalent circuit allotted only to the same, particular cell for exclusive use. As a matter of fact, the locus of bioelectrical impedance vectors actually measured is given by an arc determined according to Cole-Cole model.

One example of arc-like locus determined from Cole-Cole model is shown in FIG. 6, in which the abscissa (X-axis) and the ordinate (Y-axis) represent the resistive component and reactive component of the bioelectrical impedance respectively. As the reactive component of the bioelectrical impedance is capacitive, and is given by a negative value, the locus of bioelectrical impedance is located below the X-axis. As the calculated locus of bioelectrical impedance is assumed to be in conformity with circular arc shape, the points of bioelectrical impedance $Z_1, Z_2, \ldots, Z_N$ actually measured in terms of frequencies $F_1, F_2, \ldots, F_N$ follow a selected part of the circumference of a circle, which is given by the following equation (1):

$$(X-a)^2+(Y-b)^2=r^2, \quad (1)$$

where "a" and "b" are the abscissa and ordinate of the center of the circle, and "r" stands for the radius of the circle. The values of "a", "b" and "r" can be given by putting the impedance values $Z_1, Z_2, \ldots, Z_N$ actually measured in terms of frequencies $F_1, F_2, \ldots, F_N$ in equation (1).

Equation (1) is rewritten in terms of "X":

$$X=a\pm\sqrt{r^2-b^2} \quad (2)$$

The X-axis traverses the circle represented by equation (1) at the intersections R0 and Rinf (R0>Rinf, which intersections can be given by equations (3) and (4):

$$R0=a+\sqrt{r^2-b^2} \quad (3)$$

$$Rinf=a-\sqrt{r^2-b^2} \quad (4)$$

Re and Ri of an equivalent circuit in FIG. 5 can be given by equations (5) and (6):

$$Re=R0 \quad (5)$$

$$Ri=R0\cdot Rinf/(R0-Rinf) \quad (6)$$

The characteristic bioelectrical impedance vector Zc appears in measurement by making an alternating current of characteristic frequency Fc to flow in the body. Its reactive component has a maximum absolute value on the locus of bioelectrical impedance. The abscissa and ordinate of the characteristic bioelectrical impedance are given by:

$$X=a \quad (7)$$

$$Y=b-r \quad (8)$$

Zc is represented by equation (9):

$$Zc=Rc+jXc=a+j(b-r), \quad (9)$$

where Rc and Xc stand for the resistive and reactive components of Zc.

Bioelectrical impedance vectors for given angular frequencies ω can be calculated on the basis of Cole-Cole model, and are given by equation (10):

$$Z(\omega) = \frac{R0 - Rinf}{1 + (j\omega\tau)^\beta}, \quad (10)$$

where $Z(\omega)$ stands for bioelectrical impedance vector for ω; and τ and β are constants. Following equation (11) results by putting 1/ωc as a substitute for τ in equation (10):

$$Z(\omega) = \frac{R0 - Rinf}{1 + (j\omega/\omega_c)^\beta}, \quad (11)$$

where ωc is equal to 2πFc. Fc and β can be calculated from equation (11) by using the measured value of bioelectrical impedance.

From the equation of the bioelectrical impedance locus, and from the derivations from measured values of bioelectrical impedance, such as R0, Rinf, Re, Ri, Zc, Rc, Xc, Fc, and such like the weight each of following body compositions can be calculated: extra-cellular water, intra-cellular water, total body water (a sum of extra-cellular water plus intra-cellular water), body fat, fat free mass (which can be obtained by subtracting the body fat from the body weight) and such like. Further, from these calculated composition weights, following variables can be obtained: a ratio between intra-cellular water content and extra-cellular water content, a ratio between extra-cellular water content and total body water content, body fat percentage and such like.

Then the proceeding goes to step 14, where the screen image of FIG. 7 appears on the display 6, showing the body weight and the index value representing the degree of edema. Any other measured value and derivations from some measured values may be presented. The index value of edema is given as a ratio between intra-cellular water content and extra-cellular water content. The index value of edema, however, can be given as extra-cellular water content, a ratio between extra-cellular water content and total body water content. Also, in FIG. 7, though body weight is shown as other relevant data to be referred to, any other data such as fat free mass may be shown.

Usually, the edema appearing during a short period, say one day to several weeks is attributable to the increase of extra-cellular water, while intra-cellular water remains almost unchanged. Accordingly a ratio of intra-cellular water to extra-cellular water falls whereas a ratio of extra-cellular water to total body water rises. The body weight increases with the increase of extra-cellular water, intra-cellular water or body fat, which contributes to the increase of the total body water as much. Also, fat free mass increases with the increase of extra-cellular water or intra-cellular water.

These findings suggest that from the index value of edema and other relevant data it is possible to determine what stage of edema the person has, and whether the amount of food has been regulated well in consideration of influence of edema on the body weight for example, follows:

assuming that the index value of edema be given by a ratio of intra-cellular water to extra-cellular water, ICW/ECW, and that the relevant data be the body weight, Wt, 1) if ICW/ECW decreases and if Wt increases, this indicates that extra attention to edema is required;
2) if ICW/ECW decreases and if Wt remains unchanged, this indicates that extra attention to edema is required, and that extra attention to malnutrition is required as insufficient amount of food has been taken;
3) if ICW/ECW remains unchanged, and if Wt increases, this indicates that the person should refrain himself from overeating as an excessive amount of food has been taken; and
4) if ICW/ECW and Wt remain unchanged, this informs that there is no fear of edema, and that the person takes an appropriate amount of food.

Assuming that the index value of edema be given by a ratio of extra-cellular water to total body water, ECW/TBW, and that the relevant data be the weight of the fat free mass, FFM, 1) if ECW/TBW increases, and if FFM increases, this indicates that extra attention to edema is required;
2) if ECW/TBW increases, and if FFM remains unchanged, this indicates that extra attention to edema is required, and that extra attention to malnutrition is required as insufficient amount of food has been taken;
3) if ECW/TBW remains unchanged, and if FFM increases, this indicates that the person should refrain himself from overeating as an excessive amount of food has been taken; and 4) if ECW/TBW and FFM remain unchanged, this informs that there is no fear of edema, and that the person takes an appropriate amount of food.

Different from the determination based on the time-related variation of the index value of edema as described above, similar determination may be made by comparing the present index value of edema with a certain reference which represents the physical condition of a wholesome body, as for instance follows: the ratio of intra-cellular water to extra-cellular water in the wholesome body is about 1 to 1.2. If the present index value of edema is lower than this value, extra attention to edema is required. In case of using a ratio of extra cellular water to total body water as the index value of edema, the normal value is about 0.45 to 0.50, and if the index value of edema is higher than this value, extra attention to edema is required.

Assuming that a person is under medical treatment such as dialysis treatment, an index value of edema used as reference needs to be determined in consideration of the physical condition inherent to the patient, affected by such medical treatment. As for a person who has a dialysis treatment every other day, ordinarily the increment of body weight due to such medical treatment is equal to 3 or less percent of the reference body weight of the patient, and it is assumed that the weight of total body water be increased so much. The particulars of the patient are: the reference body weight 50 kg; the total body water 30 kg; intra-cellular water 15 kg; and extra-cellular water 15 kg. For these particulars of the patient when one kind of index value of edema (the ratio of intra-cellular water to extra-cellular water) is used as reference, it is about 0.91. When another kind of index value of edema (the ratio of extra-cellular water to the total body water) is used as reference, it is about 0.52. For the former case the tendency of index value of edema decreasing below 0.91 requires extra attention to edema whereas for the latter case the tendency of index value of edema increasing above 0.52, requires extra attention to edema.

The average of all previous index values of edema and the average of all the previous body weight values may be used as the reference index value of edema and the reference body weight respectively. Then, what stage of edema the person has and whether the amount of food has been regulated well may be determined by comparing the present index value of edema and the present body weight with the reference index value of edema and the reference body weight. To meet this average-based determination the edema measuring apparatus may be so modified that: the index value of edema and body weight may be stored in an auxiliary memory 5 at each measurement; the average index value of edema and the average body weight may be calculated from these stored data; what stage of edema the person has and whether the amount of food has been regulated well may be determined by comparing the present index value of edema and the present body weight with the average index value of edema and the average body weight; and the determinations thus made are given in the display by using arrows or facelike marks as for instance, follows: "↑" or "(ô)" indicates ---fairly good---; "→" or "(•__•)" indicates ---good---, and "↓" or "(T_T)" indicates ---bad---.

At step 15 the values of measurement, derivations therefrom and other data are stored in an auxiliary memory 5. Such data may be transferred to external devices via the external input-output interface 7.

Figure 8:
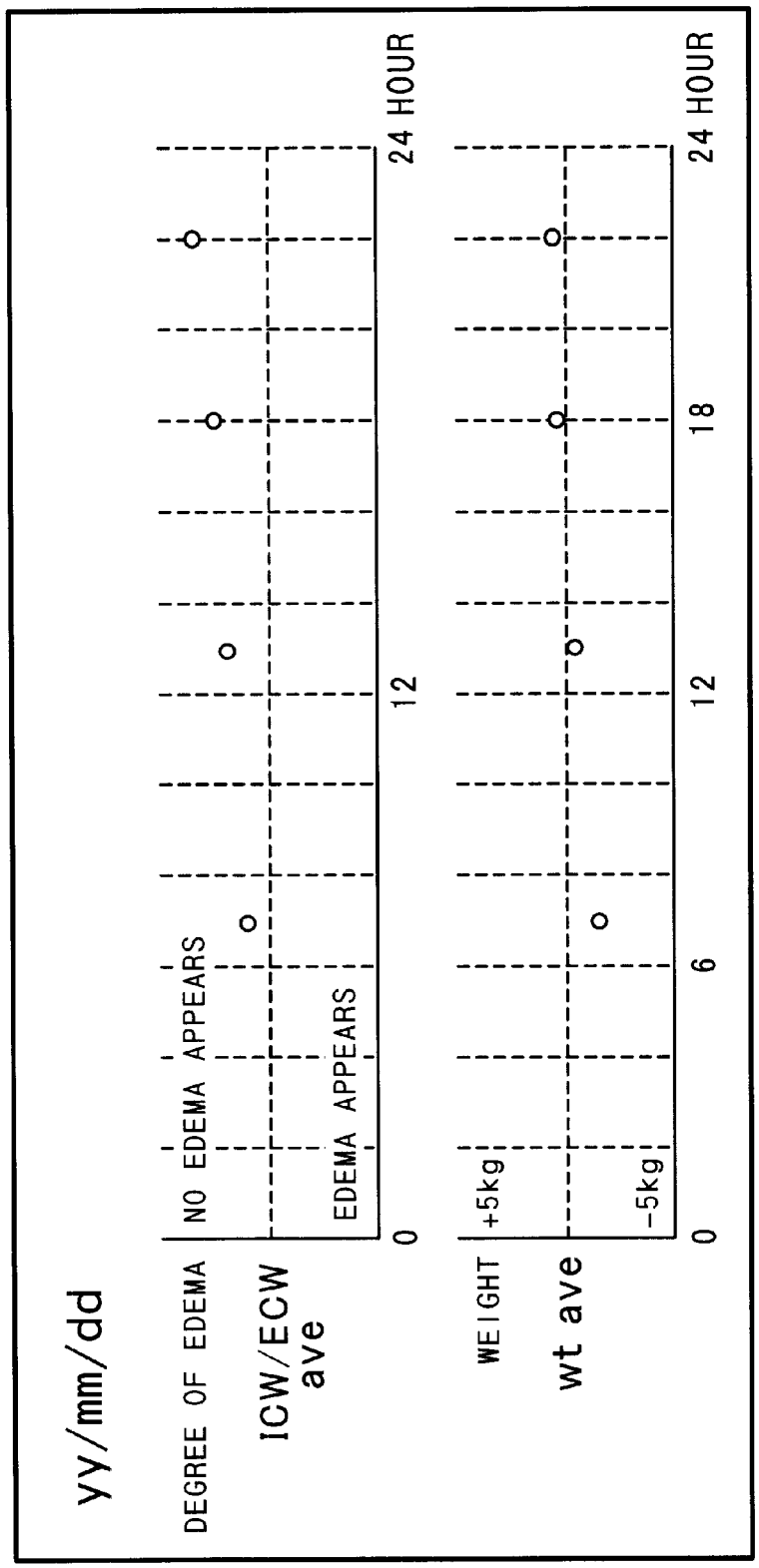
FIG. 8 illustrates a screen image showing one example of retro-graphic representation of the values of latest and preceding measurements effected in a 24 hour period counted from the latest measurement.
Figure 9:
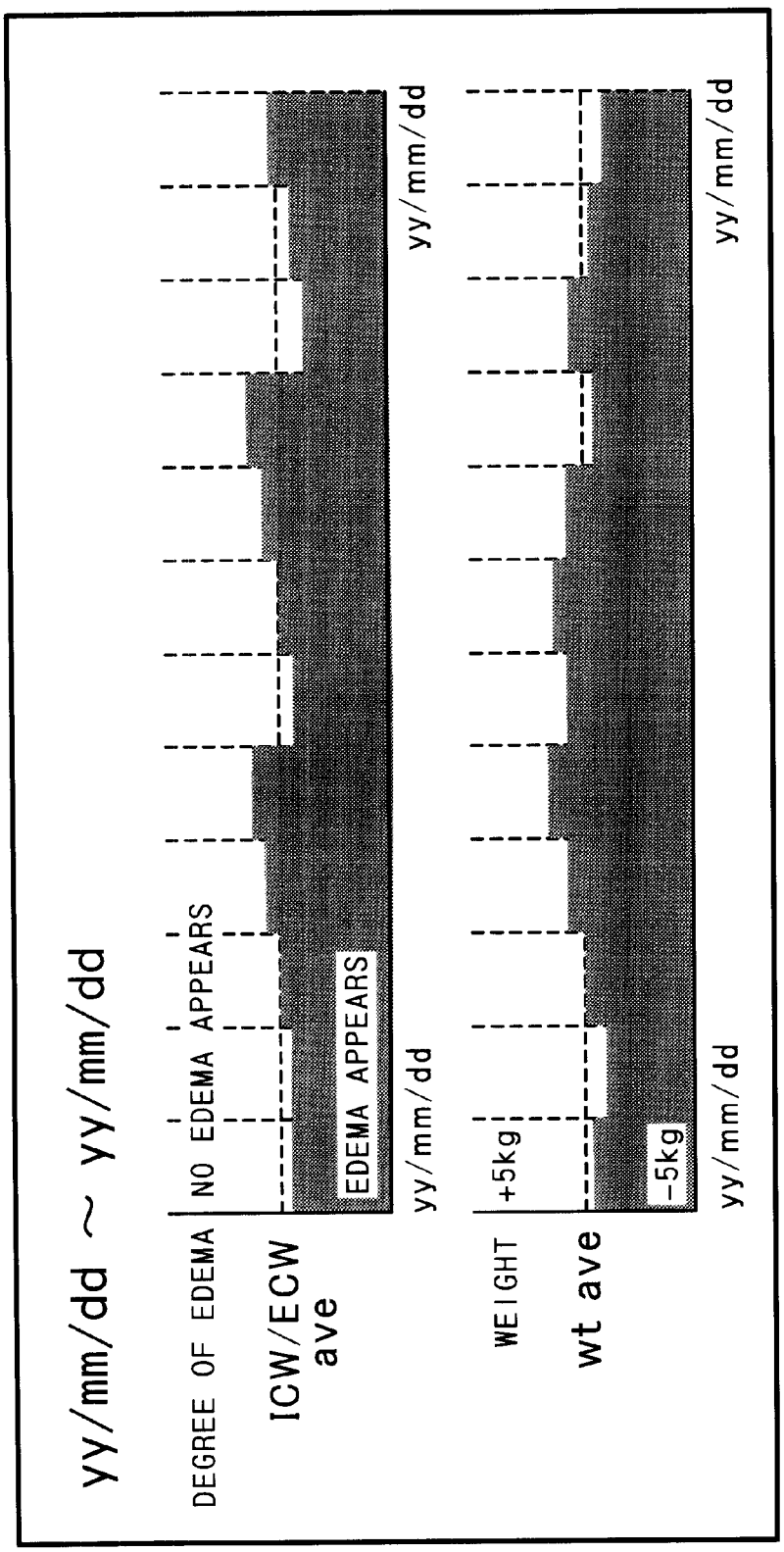
FIG. 9 illustrates a screen image showing one example of retro-graphic representation of all measurements which were effected before.

At step 16, if the re-measuring key is depressed, the proceeding goes back to step 11, from which another series of actions taken for measurement are executed again. If the graphic representation key is depressed instead of the re-measuring key, the proceeding goes to step 17, where the screen image of FIG. 8 or 9 appears on the display. FIG. 8 shows retro-graphic representation of the index values of edema and the body weights measured in the latest and preceding measurements effected in a 24 hour period counted from the latest measurement. FIG. 9 shows retro-graphic representation of the index values of edema and the body weights measured in all measurements which were effected before.

In these graphs the ratio of intra-cellular water to extra-cellular water (ICW/ECW) is used as the index value of edema, and the body weight (Wt) is used as the relevant data to be referred to. The extra-cellular water (ECW) or the ratio between extra-cellular water and total body water (ECW/TBW) may be used as the index value of edema, and the fat free mass may be used as the relevant data to be referred to.

In FIG. 8 two or more retro-graphic representations of the values of measurements which were effected for 24 hours and for a long period such as week or month may be selected for display, thereby permitting the surveying of historical variation of the variables for an elongated length of time.

Referring to FIG. 9 again, the length of time spanning from the outset to the latest measurement is divided in 12 equi-divisions, and each average of the index values of edema calculated in each of the equi-divisions is displayed as one value so as to display 12 values in total. Preferably the number of divisions are 10 to 15. For example, in case that the measurements were effected for one month, the whole month is preferably divided every 3 days apart to provide 10 equi-divisions. The six month measurement span may be divided every half a month apart to provide 12 equi-divisions.

Then at step 18, the depressing of the ending key allows the apparatus to turn off, finishing the measurement.

The following description returns to and begins with step 8. At step 8 the key "2" allotted to "graphical representation" is depressed, and then the proceeding goes to step 19, where data and parameters for display are retrieved from the auxiliary memory 5. Then, at step 17 the desired graphical representations of predetermined configuration such as shown in FIG. 8 or 9 appear.

Likewise, at step 8 the key "3" allotted to "communication" is depressed, and then the proceeding goes to step 20, where selected data and parameters are retrieved from the auxiliary memory 5. At step 21 these data and parameters are transmitted to a selected external data processor via telephone lines. Such data may include: the values of bioelectrical impedance and other measured values (voltage, phase difference therebetween, and date and time of measurement, etc.); derivations therefrom (R0, Rinf, Re, Ri, Zc, Rc, Xc, or Fc, etc.); weights of body compositions (intra-cellular water, extra-cellular water, total body water, fat free mass or body fat, etc.); a variety of index values of edema (extra-cellular water, ratio between intra-cellular water and extra-cellular water, ratio between extra-cellular water and total body water, etc.); personal particulars (identification number, name, sex, age, height, body weight, etc.) and so on.

Such communication is useful in edema-monitoring at home for an outpatient who is under medical treatment. Thanks to such communication capability, the patient measures the index value of edema by using the edema measuring apparatus at home so that he may transmit the required data such as the so measured index values of edema to the external data processor installed in the hospital at a distant place. Thus a doctor can realize the degree of edema of the patient accurately, permitting him to appoint a time for next treatment appropriately. A significant contribution to medical activity may be expected.

The external data processor may execute a required process on data received from the edema measuring apparatus, and the external data processor may transmit the processing's result to the edema measuring apparatus. Receiving the result the edema measuring apparatus may show the result on the display.

Next, an edema measuring apparatus according to the second embodiment which uses an AC signal generator capable of providing an alternating current of single frequency at its output terminals will be described.

Figure 10:
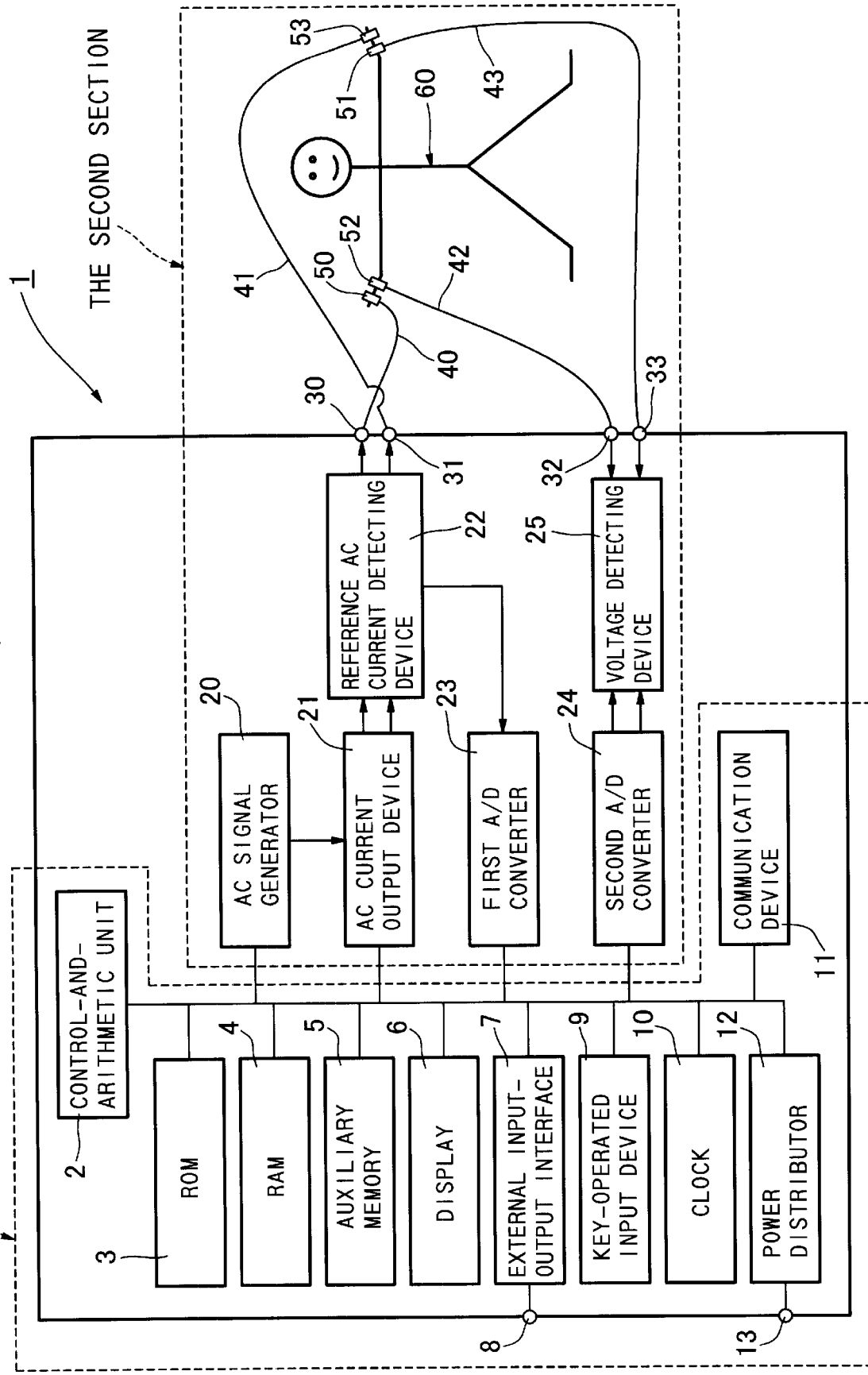
FIG. 10 illustrates major parts of an edema measuring apparatus according to a second embodiment of the present invention.
Figure 11:
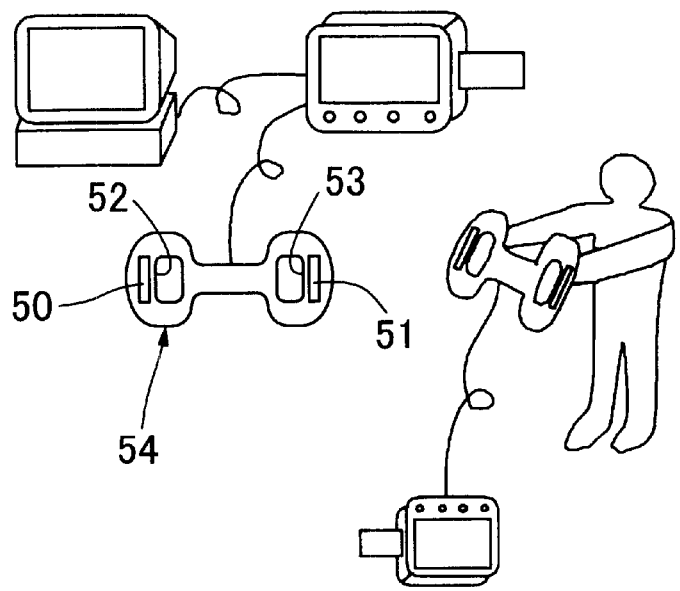
FIG. 11 illustrates an edema measuring apparatus equipped with a hand-held type of electrode assembly.

FIG. 10 illustrates major parts of the edema measuring apparatus, which is different from the edema measuring apparatus of FIG. 1 using a multi-frequency AC signal generator in that an alternating current of one frequency is supplied to a person. In this particular example the person stands upright, permitting the measuring of the bioelectrical impedance appearing between two points selected on both hands. Referring to FIG. 11, the edema measuring apparatus is equipped with a hand-held type of electrode assembly 54, which comprises paired measuring current applying electrodes 50 and 51 and another paired voltage measurement electrodes 52 and 53. These electrodes are fixed apart from each other on the assembly 54.

Figure 12:
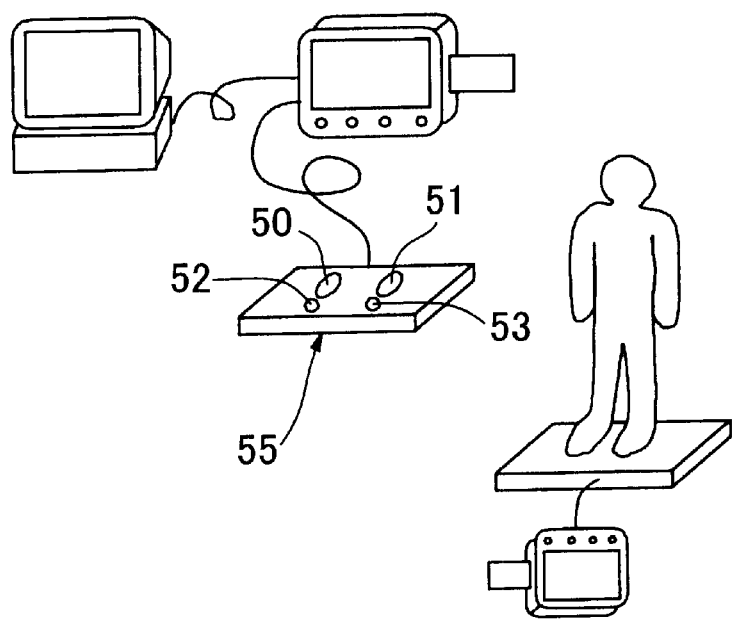
FIG. 12 illustrates another edema measuring apparatus equipped with a sole-contacting type of electrode assembly.

Instead of measuring the bioelectrical impedance appearing between hands, the bioelectrical impedance appearing between one and the other foot may be measured by using a sole-contacting type of electrode assembly 55, as shown in FIG. 12. It has paired measuring current applying electrodes 50 and 51 and another paired voltage measurement electrodes 52 and 53 fixed on the assembly 55.

The degree of edema can be measured in the same way as above. Specifically a series of actions taken for the measurement follows the flowchart of FIG. 2, provided that at step 12 an alternating current of single frequency $F_1$ in place of the multiple frequencies is made to flow in the body to measure the bioelectrical impedance value and the phase difference between the applied alternating current and the measured voltage appearing between two points selected on the body.

Figure 13:
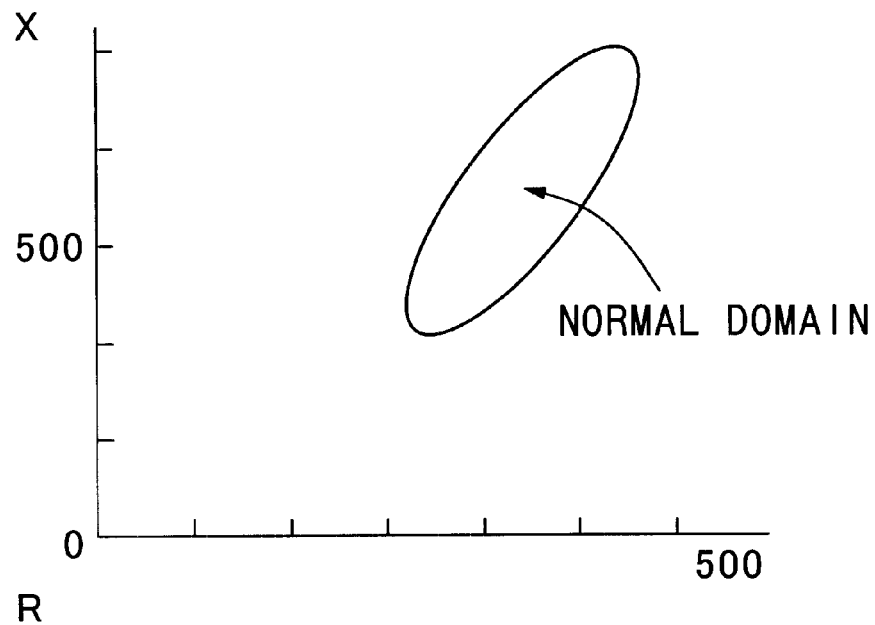
FIG. 13 shows a certain domain in which normal values of bioelectrical impedance can be given in terms of resistive and reactive components.

At step 13 a decision is made on the bioelectrical impedance value $Z_1$ measured for the frequency $F_1$ in terms of whether it is in a normal impedance domain (see the graph of FIG. 13 plotted for 50 KHz, abscissa: resistive value R and ordinate: reactive value X), in which normal values of bioelectrical impedance would exist. If the bioelectrical impedance value $Z_1$ is not within the domain, it is supposed to be abnormal, and then, some variables relating to the locus of bioelectrical impedance vectors are obtained from the measured value of bioelectrical impedance as follows.

Figure 14:
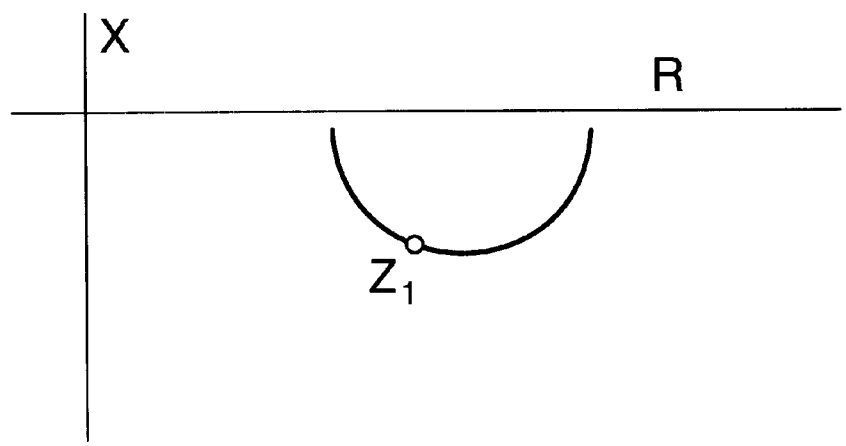
FIG. 14 shows one example of locus which the points of bioelectrical impedance vectors follow.

As described the above, the locus of bioelectrical impedance vectors actually measured is assumed to be in conformity with circular arc shape. The bioelectrical impedance $Z_1$ is located on a selected point of the circumference of the circle as shown in FIG. 14, in which the abscissa (X-axis) and the ordinate (Y-axis) represent the resistive component and reactive component of the bioelectrical impedance respectively.

A bioelectrical impedance value for a given angular frequency $\omega F$ is given by:

$$Z(\omega F) = \frac{1}{1 + (j\omega F/\omega 0)^\beta}, \quad (12)$$

where $\omega 0$ and $\beta$ are constants. Following equation (13) results by substituting 1 for $\beta$ in equation (12):

$$Z(\omega F) = \frac{1}{1 + j\omega F/\omega 0} \quad (13)$$

Figure 15:
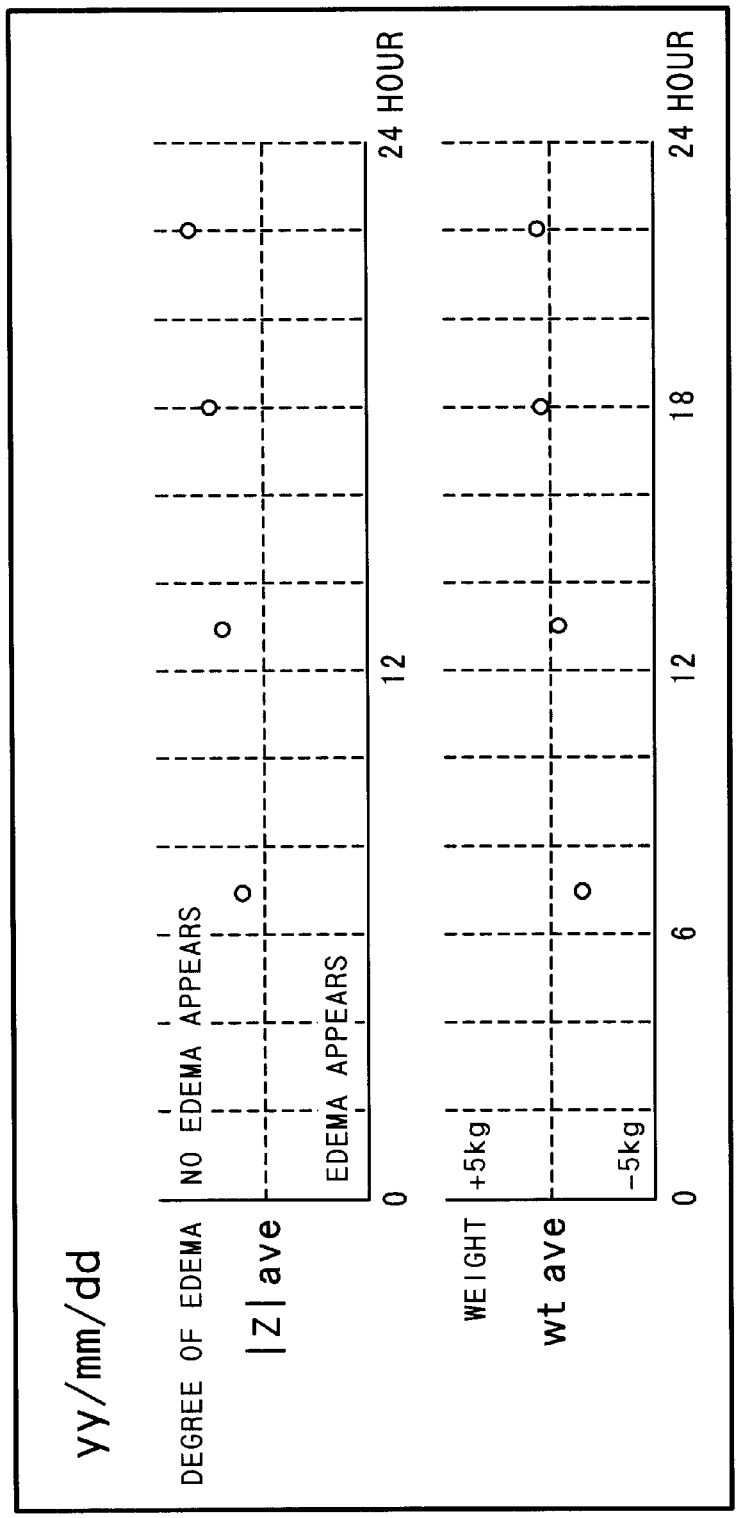
FIG. 15 illustrates a screen image showing one example of retro-graphic representation of the values of latest and preceding measurements effected in a 24 hour period counted from the latest measurement.
Figure 16:
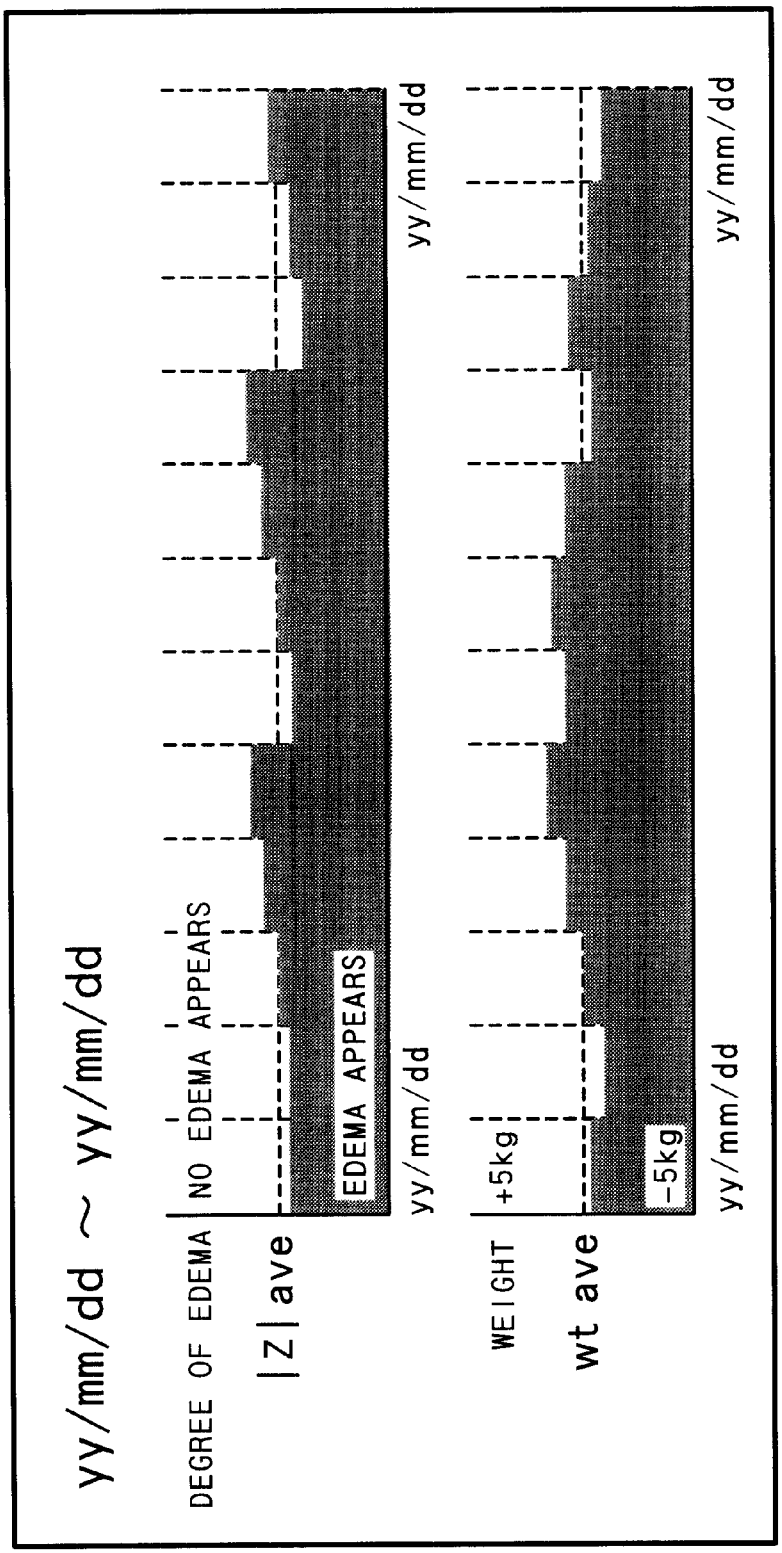
FIG. 16 illustrates a screen image showing one example of retro-graphic representation of all measurements which were effected before.

From the measured value of bioelectrical impedance and the measured phase difference, the weights of body compositions such as total body water, fat free mass, body fat, and such like can be calculated. From these calculated composition weights, variables such as body fat percentage can be obtained. Further, an index value of edema is calculated from the measured phase difference and resistive value, which resistive value is obtained from the applied alternating current and the measured voltage value. The so calculated index value of edema appears on the display 6 at step 14 and at step 17. For instance, the screen images of FIGS. 15 and 16 alternately appear at step 17.

Figure 17:
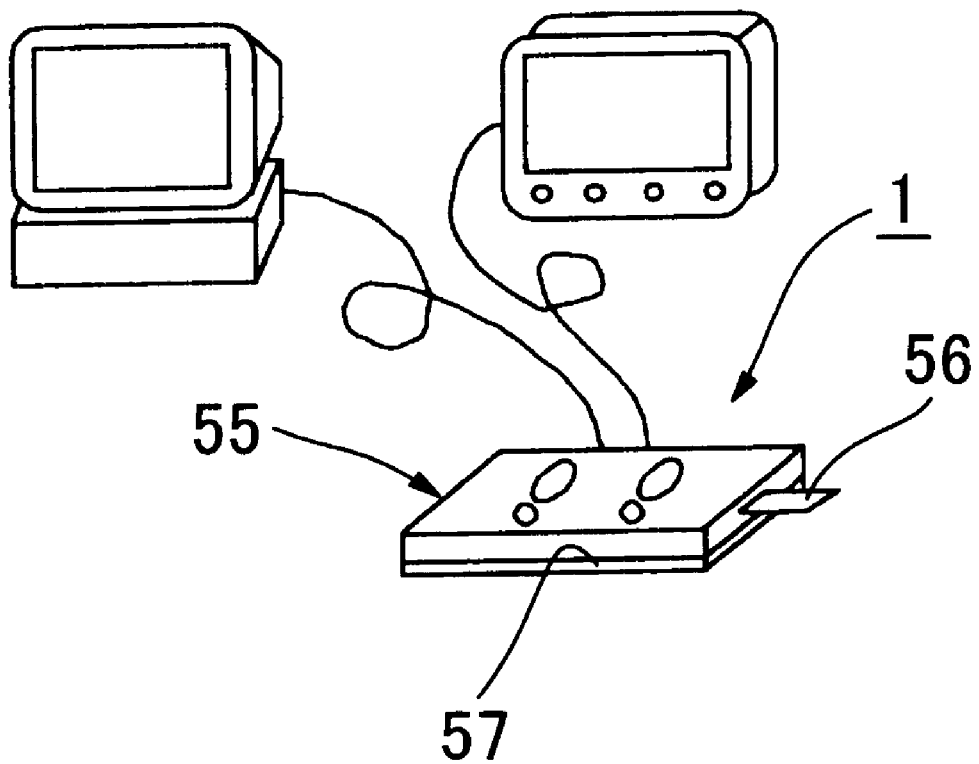
FIG. 17 illustrates an edema measuring apparatus with the scales and an associated memory card.

The edema measuring apparatus 1 may be so modified that desired pieces of information such as measured values, some variables derived therefrom, weighs of body compositions, index values of edema and personal particulars may be written to memory cards 56 shown in FIG. 17 and other portable record mediums, to which other data processors can access. Availing himself of this function, the patient at home can record the desired pieces of information on a portable record medium without clerical, producing it at hospital.

The edema measuring apparatus may be incorporated into a portable terminal.

Figure 18:
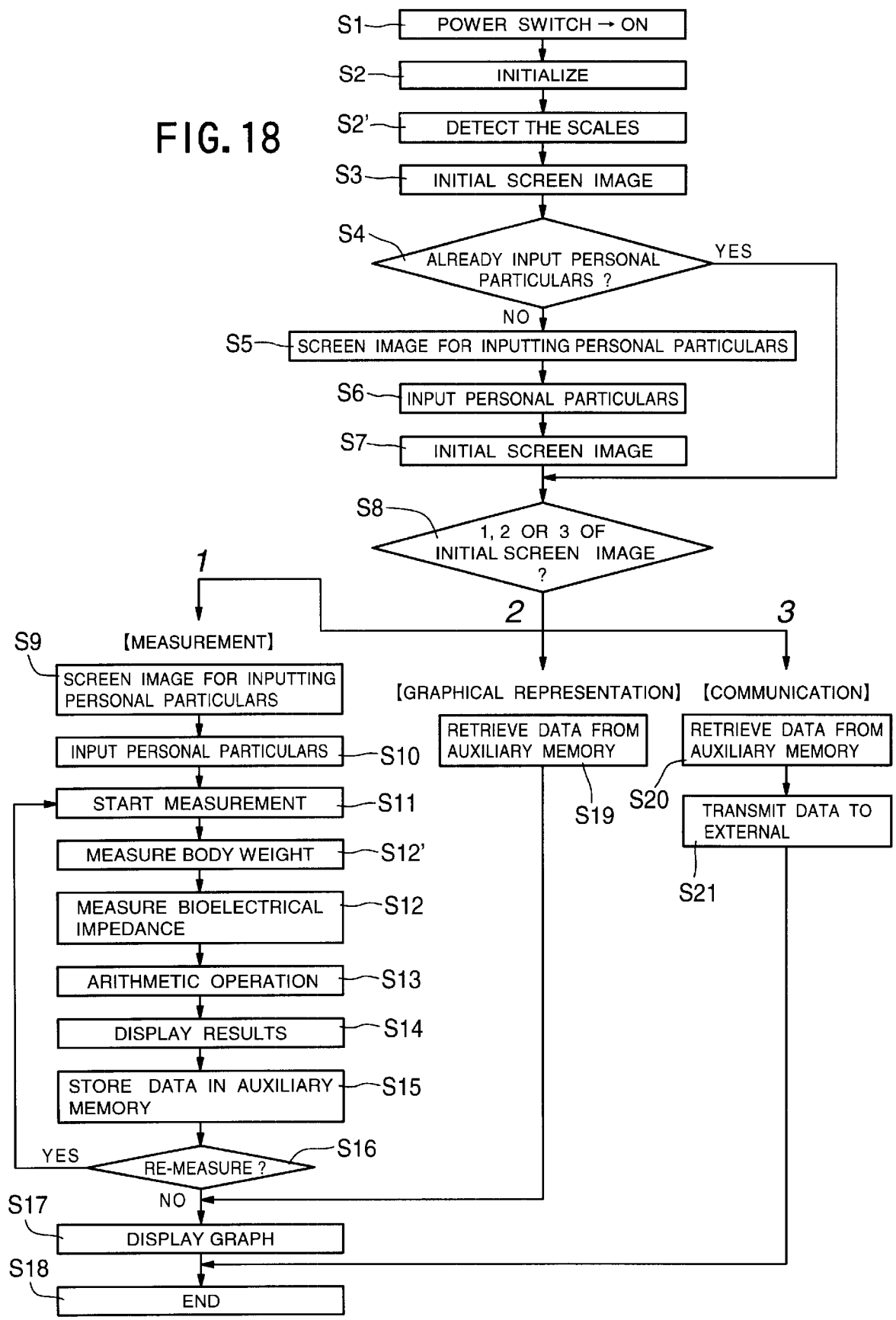
FIG. 18 is a flowchart illustrating a series of actions taken for measuring the degree of edema when using the edema measuring apparatus of FIG. 17.

The sole-contacting type of electrode assembly 55 may be easily modified to function as the scales 57 shown in FIG. 17. With this modification the edema measuring apparatus may follow the flowchart of FIG. 18, making it unnecessary for the user to input his weight with the aid of the key-operated input device 9 at step 6 or 10 as described above. Specifically at step 2' it is confirmed that the sole-contacting type of electrode assembly 55 capable of weighing one's weight is connected to the external input-output interface 7. The body weight is measured at step 12'.

In the embodiments as described above the hand-to-foot, hand-to-hand, or foot-to-foot bioelectrical impedance is measured. As a matter of course, two or more different bioelectrical impedances among them are measured one after another to locate on which part of the body an edema appears.

As may be understood from the above, the edema measuring method and apparatus can measure the degree of edema with accuracy and easiness by putting at least two pairs of electrodes on different locations selected in the body; making an alternating current to flow in the body via one pair of electrodes; measuring voltage appearing between the other pair of electrodes; calculating impedance on the basis of the supplied alternating current and the measured voltage; and calculating an index value representing the degree of edema on the basis of the impedance.

What is claimed is:

1. An apparatus which is capable of measuring a degree of edema of a person characterized in that it comprises:
   at least two pairs of electrodes to be put on selected locations in the body of the person;
   an alternating current supplying device which supplies alternating current to one pair of the electrodes;

a voltage measuring device which measures the voltage appearing between the other pair of electrodes;

an arithmetic unit which calculates impedance on the basis of the supplied alternating current and the determined voltage, and calculates an index value representing the degree of edema on the basis of the so calculated impedance; and an estimating device which determines the degree of edema the person has from the calculated index value of edema and a body weight or fat free mass of the person.

2. An apparatus which is capable of measuring a degree of edema of a person characterized in that it comprises:

at least two pairs of electrodes to be put on selected locations in the body of the person;

an alternating current supplying device which supplies alternating current to one pair of the electrodes;

a voltage measuring device which measures the voltage appearing between the other pair of electrodes;

an arithmetic unit which calculates impedance on the basis of the supplied alternating current and the determined voltage, and calculates a preset index value representing the degree of edema on the basis of the so calculated impedance; and an estimating device which determines a stage of edema of the person by comparing the preset index value of edema with an average of index values of edema previously calculated.

3. An apparatus which is capable of measuring a degree of edema of a person characterized in that it comprises:

at least two pairs of electrodes to be put on selected locations in the body of the person;

an alternating current supplying device which supplies alternating current to one pair of the electrodes;

a voltage measuring device which measures the voltage appearing between the other pair of electrodes;

an arithmetic unit which calculates impedance on the basis of the supplied alternating current and the determined voltage, and calculates an index value representing the degree of edema on the basis of the so calculated impedance; and a display which shows a series of index values of edema previously calculated, representing how the index value of edema has varied.

4. An apparatus which is capable of measuring a degree of edema of a person characterized in that is comprises:

at least two pairs of electrodes to be put on selected locations in the body of the person;

an alternating current supplying device which supplies alternating current to one pair of the electrodes;

a voltage measuring device which measures the voltage appearing between the other pair of electrodes;

an arithmetic unit which calculates impedance on the basis of the supplied alternating current and the determined voltage, and calculates an index value representing the degree of edema on the basis of the so calculated impedance; and a communication device which transmits to other data processors at least one piece of information selected among measured voltage, measured phase difference, some derivations therefrom, the calculated index value of edema, a determined stage of edema of the person, and personal particulars of the person.

5. An apparatus according to any of claims 1 to 4, wherein:

the alternating current supplying device supplies a plurality of alternating currents of different frequencies to said one pair of electrodes; and the voltage measuring device measures the voltage appearing between said the other pair of electrodes each time an alternating current of selected frequency is supplied, allowing the arithmetic unit to calculate the impedance values on the basis of each alternating current and corresponding voltage and to calculate the index value of edema on the basis of the so calculated impedance values.

6. An apparatus according to claims 1 to 4, wherein the index value of edema includes a ratio of intra-cellular water to extra-cellular water or inversely, or a ratio of extra-cellular water to total body water or inversely.

7. An apparatus according to any of claims 1 to 4, wherein it further comprises a phase difference measuring device which measures the phase difference between the supplied alternating current and the measured voltage, whereby the arithmetic device may calculate the index value of edema on the basis of the phase difference and the resistance value calculated from the alternating current and the voltage when an alternating current of single frequency is supplied to said one pair of electrodes.

8. An apparatus according to any of claims 1 to 4, wherein it further comprises an estimating device which determines the stage of edema of the person based on the calculated index value of edema and other relevant data.

9. An apparatus according to claim 1, wherein the index value of edema is a ratio of intra-cellular water to extra-cellular water, and wherein said estimating device determines that the person should reduce food intake because an excessive amount of food has been taken when the ratio decreases and the body weight increases.

10. An apparatus according to claim 1, wherein the index value of edema is a ratio of intra-cellular water to extra-cellular water, and wherein said estimating device determines that extra attention to malnutrition is required due to an insufficient amount of food being taken when the ratio decreases and the body weight remains unchanged.

11. An apparatus according to claim 1, wherein the index value of edema is a ratio of intra-cellular water to extra-cellular water, and wherein said estimating device determines that the person takes an appropriate amount of food when the ratio and the body weight remain unchanged.

12. An apparatus according to any of claims 1, 3, 4, 9, 10 or 11, wherein said estimating device further determines whether an amount of food has been regulated well based on the calculated index value of edema and other relevant data.

13. An apparatus according to claim 3, wherein said other relevant data is a body weight or fat free mass of the person.

14. An apparatus according to any of claims 1 to 4, wherein it further comprises a second estimating device which determines the stage of edema of the person by comparing the calculated index value of edema with a reference value which represents an index value of edema of a person in normal physical condition.

15. An apparatus according to claim 14, wherein it further comprises a third estimating device which determines the stage of edema of the person by comparing the index value of edema with an average of the index values of edema previously calculated.

16. An apparatus according to claim 15, wherein it further comprises a display which shows the calculated index value of edema and/or the determined stage of edema of the person.

17. An apparatus according to claim 16, wherein said display shows a series of index values of edema previously calculated, representing how the index value of edema has varied.

18. An apparatus according claim 17, wherein said display shows 10 to 15 averages of index values of edema, each average representing the average of the index values calculated in each of 10 to 15 equi-divisions into which the length of time spanning from a first measurement to the latest measurement is divided.

19. An apparatus according to claim 18, wherein it further comprises a communication device which transmits to other data processors at least one piece of information selected among measured voltage , measured phase difference, some derivations therefrom, the calculated index value of edema, a determined stage of edema of the person, and personal particulars of the person.

20. An apparatus according to claim 19, wherein said communication device receives the results of a given process executed on said information in said other data processors.

21. An apparatus according to claim 20, wherein it further comprises a writing device which writes one piece of information selected among measured voltage, measured phase difference, some derivations therefrom, the calculated index value of edema, a determined stage of edema of the person, and personal particulars of the person.

* * * * *